United States Patent [19]

Chang

[11] Patent Number: 4,489,209

[45] Date of Patent: Dec. 18, 1984

[54] SEPARATION OF AMINES BY PREFERENTIAL AQUEOUS SALT EXTRACTION

[75] Inventor: Tzu-Ching Chang, Wilmington, Del.

[73] Assignee: E. I. Du Pont de Nemours and Company, Wilmington, Del.

[21] Appl. No.: 331,894

[22] Filed: Dec. 17, 1981

[51] Int. Cl.³ ............................................. C07C 85/26
[52] U.S. Cl. ..................................... 564/425; 564/438
[58] Field of Search ................................ 564/425, 438

[56] References Cited

U.S. PATENT DOCUMENTS

| | | | |
|---|---|---|---|
| 1,663,251 | 3/1928 | Gubelmann et al. | 564/425 |
| 1,884,776 | 10/1932 | Lubs et al. | 564/425 X |
| 1,998,795 | 4/1935 | Tinker et al. | 564/425 X |
| 2,009,757 | 7/1935 | Bentley et al. | 260/130.5 |
| 2,031,666 | 2/1936 | Perkins | 564/425 |
| 2,069,546 | 2/1937 | Carswell | 564/425 |
| 2,732,393 | 1/1956 | Hardy | 564/425 X |
| 4,174,351 | 11/1979 | Shoffner | 260/582 |

OTHER PUBLICATIONS

Dissociation Extraction Part I: General Theory, Anwar, et al., Trans., Instn. Engrs., vol. 49, 1971.
Separation of Close Boiling Substituted Phenols by Dissociation Extraction, Wadekar, et al., J. Chem. Tech. Biotechnol. 31, pp. 279-284 (1981).

*Primary Examiner*—Paul F. Shaver

[57] ABSTRACT

A process of separating amines having different basicity constants is disclosed. The more reactive amine is converted to a salt which is extracted with water in a multiple stage countercurrent extractor. The salt form of the amine is converted to the free amine. In a preferred aspect of the invention the amine salt is an amine sulfite which can be converted to free amine and sulfur dioxide. The sulfur dioxide can be reused to generate more amine sulfite. The more reactive amine is then separated from the water and part of it recovered. The remainder of the more reactive amine is recycled to the countercurrent extractor. The less reactive amine is removed from the countercurrent extractor in the free amine state as an organic phase along with any organic solvent that is used. Part of the less reactive amine is recovered from the system while the remainder is converted to a salt and an aqueous solution thereof recycled to the countercurrent extractor.

6 Claims, 2 Drawing Figures

SEPARATION OF AMINES BY PREFERENTIAL AQUEOUS SALT EXTRACTION

BACKGROUND OF THE INVENTION

1. Field of The Invention

The present invention relates to a process for the separation of two or more amines of different basicity. The more reactive amine is preferentially reacted with an acid and the resulting salt is extracted with water leaving behind an organic phase comprising the less reactive amine.

2. Prior Art

Separation of the weak organic bases 3- and 4-picoline by contacting a solution of the two bases in an organic solvent with an aqueous phase containing a stoichiometric deficiency of a strong acid in relationship to the two bases so that the two bases will compete for the available acid is disclosed by "Dissociation Extraction Part I: General Theory", Anwar et al, Trans. Instn. Chem. Engrs., Vol. 49, 1971. The isomer with the higher dissociation constant, that is the stronger base will react preferentially with the strong acid forming a salt in the aqueous phase thus causing an enrichment of the organic phase with respect to the weaker base. The article claims that, by applying this principle to a multistage countercurrent operation, products of high purity can be obtained.

Some mixtures of substituted phenols, which are difficult to separate by established methods such as distillation or crystallization, have been separated by dissociation extraction as disclosed in "Separation of Close Boiling Substituted Phenols by Dissociation Extraction," Wadekar et al, J. Chem. Tech. Biotechnol. 31, pp 279–284 (1981).

In the past amines which are dissimilar in nature by virtue of possessing different substituents, different structures or position isomers have been selectively separated by various techniques. One such technique is to treat the mixture of amines such as a mixture of m-toluidine and p-toluidine with a reactive carbonyl compound and an acid. The m-toluidine will form an imine while the p-toluidine will form an acid salt. The two can then be recovered as separate aqueous and organic phases. Such a technique is disclosed in U.S. Pat. No. 4,174,351.

SUMMARY OF THE INVENTION

The present process relates to a process for separating a plurality of amines at least two of which have a significant difference in basicity in which a portion of the amines are reacted with sulfurous acid to form a sulfite of the more reactive amines. The sulfite form of the amine is extracted with water while the unreacted amines remain in an organic phase which may comprise a water immiscible organic solvent in addition to the amine. The extraction is done in multiple stages. The amine sulfite in the aqueous phase is converted to the amine form and recovered such as by decantation of phases while any organic solvent in the organic phase is removed such as by distillation.

DETAILED DESCRIPTION OF THE DRAWINGS

Figure 1:
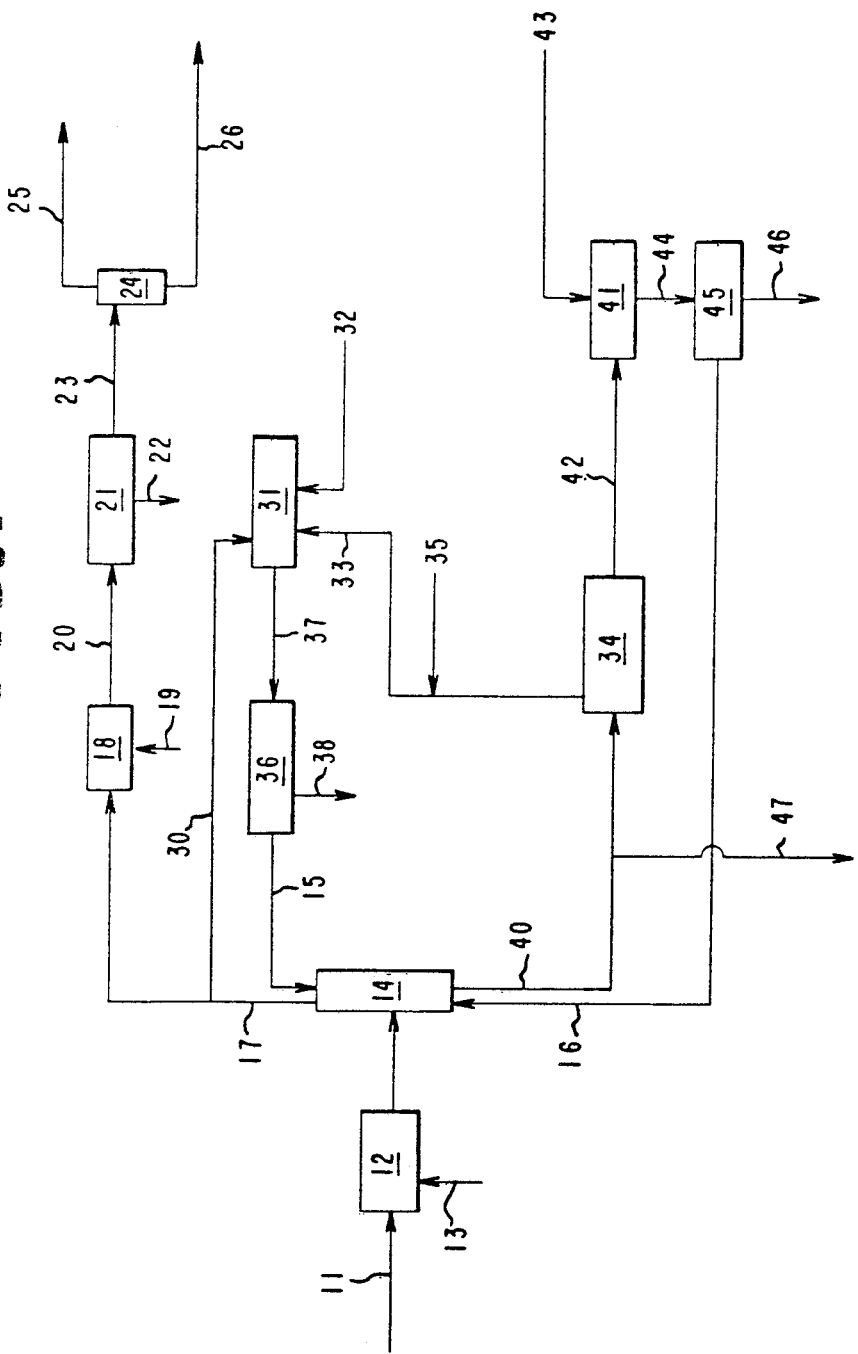
FIG. 1 is a flow sheet of a primary separation unit of the present invention.

Referring now to FIG. 1, a mixture of amines is fed in line 11 to feed dissolver 12 where the mixture of amines optionally is dissolved in an organic solvent which organic solvent is fed to dissolver 12 by means of line 13. The amines and optional organic solvent are fed to multiple stage extraction unit 14. An aqueous solution of a sulfite salt of the least reactive amine is fed through line 15 to multiple stage extraction unit 14. The more reactive amine or amines either neat or in an organic solvent are fed to multiple stage extraction unit 14 by means of line 16. The less reactive amine in its free form either neat or dissolved in whatever solvent is removed from multiple stage extraction unit 14 by means of line 17. The less reactive product stream is fed to washer 18 where the amine is contacted with an aqueous base such as aqueous sodium hydroxide which is fed to washer 18 by line 19. The aqueous base and amine is then sent via line 20 to decanter 21 where the product amine is separated from the aqueous base which aqueous base is removed from decanter via line 22. The amine (optionally) is sent via line 23 to column 24 where any solvent used is separated and removed in line 25 and the product amine is recovered in line 26. A side stream 30 of less reactive amine and optional solvent is taken from line 17 and fed to neutralizer 31. Water, either from one of the decanters or fresh water is fed to neutralizer 31 by line 32. Sulfur dioxide is sent to neutralizer 31 via line 33. Sulfur dioxide in line 33 is recycle sulfur dioxide from sulfur dioxide regenerators 34 and 56 mixed with fresh makeup from line 35. If the amine or amines in line 30 contain a solvent the effluent from neutralizer 31 is fed to decanter 36 via line 37 where the solvent phase is separated and removed in line 38 prior to being sent to multiple stage extraction unit 14 via line 15, otherwise the effluent from neutralizer 31 is sent directly to multiple extraction unit 14.

The more reactive amine or amines in the form of sulfite salt in aqueous solution is removed from multiple stage extraction unit 14 in line 40 and sent to sulfur dioxide regenerator 34. The amine sulfite salt can readily be broken down by a simple means such as by heating and then sulfur dioxide is recycled to neutralizer 31. The freed amine or amines from sulfur dioxide regenerator 34 are fed to extractor 41 via line 42 where organic solvent if desired is added from line 43. The effluent from extractor 41 is fed through line 44 to decanter 45. The aqueous phase is removed from decanter 45 in line 46, and the stronger amine or amines and optional organic solvent fed through line 16 to multiple stage extractor 14. The product more reactive amine or amines are removed from line 40 in line 47. If only one amine is in line 47 it is freed from its salts by heating to remove sulfur dioxide and the organic amine phase separated from the aqueous phase by decantation.

Figure 2:
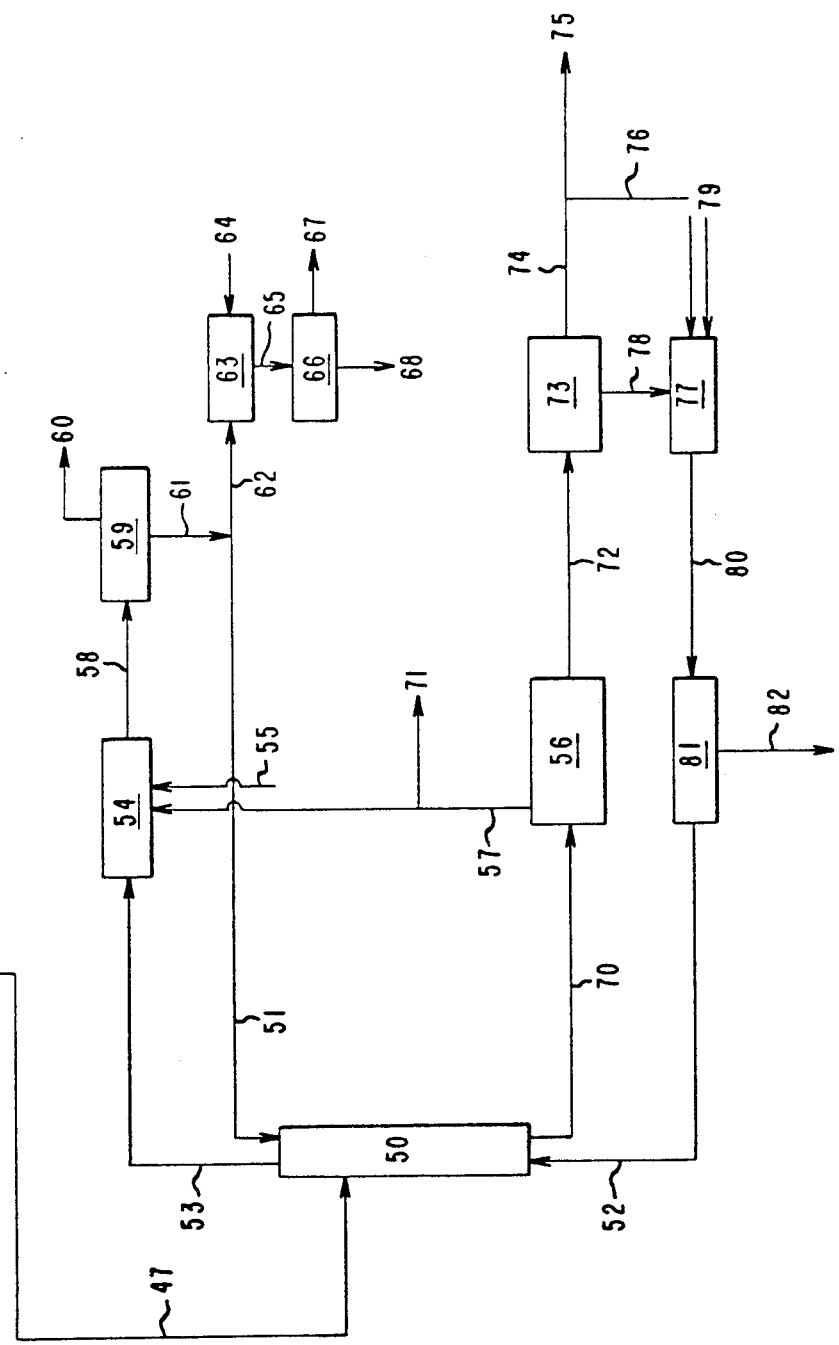
FIG. 2 is a flow sheet of a secondary separation unit of the present invention.

If there is more than one amine in line 47 it is treated further. Referring now to FIG. 2, line 47 from FIG. 1 containing two amines in the form of sulfite salts in aqueous solution which are more reactive than the amine separated in FIG. 1 are fed to multiple stage extraction unit 50. A recycle stream comprising an aqueous sulfite salt solution of the less reactive amine from line 47 is fed to multiple stage extraction unit 50 by line 51. A recycle stream of the more reactive amine from line 47 and optional organic solvent is fed to multiple stage extraction unit 50 by line 52. The less reactive amine from line 47 and optionally organic solvent are removed in line 53 from multiple stage extraction unit 50 and sent to neutralizer 54. Water, either from a decanter or fresh makeup water is fed to neutralizer 54 via line 55. Regenerated sulfur dioxide from sulfur dioxide regenerator 56 is fed to neutralizer 54 by line 57. Additionally fresh acid can be fed to neutralizer 54. The effluent from neutralizer 54 is fed via line 58 to decanter 59 where the solvent, if any, is removed via line 60. The aqueous amine salt solution from decanter 59 is removed in line 61 where it is split into line 62 and line 51. The aqueous salt solution in line 62 is fed to basifier 63. An aqueous base solution is fed to basifier 63 in line 64. The effluent from basifier 63 is fed via line 65 to decanter 66 where it is separated into a free amine product phase which is removed via line 67 and an aqueous phase in line 68. An aqueous solution of the salt of the more reactive amine from line 47 is removed from multiple stage extraction unit 50 in line 70 and fed to sulfur dioxide regenerator 56. Excess regenerated sulfur dioxide is removed from line 57 by line 71 where it is sent to storage and used to augment makeup acid fed to the system in line 35. The resulting free amine and water is fed by line 72 to decanter 73. The free amine is removed from decanter 73 in line 74. Product amine is recovered from line 74 in line 75 while the remaining amine is recycled in line 76 to extractor 77. The aqueous phase separated in decanter 73 is fed by line 78 to extractor 77. Optionally solvent is fed by line 79 to extractor 77. The effluent from extractor 77 is fed by line 80 to decanter 81 where the aqueous phase is removed in line 82. The remaining amine and optional solvent is fed by line 52 to multiple stage extraction unit 50. If the amine product in line 75 contains more than one amine, one or more additional stage such as shown in FIG. 2 can be used to separate such amines.

The above description of the drawings assumes that the density of the organic phase in each of the two extraction columns is lower than the density of the aqueous phase so that the organic phase flows upward in the extraction column, and the aqueous phase flows downward. If the density of the organic phase is higher than the aqueous phase, then the organic phase will flow downward in the extraction column, and the less base amine will be removed from the bottom of the extraction column, while the more base amine or amines, in the form of sulfite salt in aqueous solution, will be removed from the top of the extraction column.

DETAILED DESCRIPTION

Generally the process of the present invention is useful in separating any organic amines which amines are essentially immiscible in water and have a basicity constant $K_B$ in the range of from $1 \times 10^{-10}$ to $20 \times 10^{-10}$. Amines which have a basicity constant below about $1 \times 10^{-10}$ such as the chloroanilines do not have sufficient basicity to react with sulfur dioxide. Regeneration of $SO_2$ from the salt formed with amines having basicities above $20 \times 10_{-10}$ such as p-phenylenediamine is not feasible due to stability of the salt. Examples of amines which may be effectively separated according to the process of this invention will include aryl amines such as o-toluidine, m-toluidine, p-toluidine, 2,4-xylidine, 2,6-xylidine, etc. It is to be understood that the aforementioned amines are only representative of the class of compounds which may be separated and that the present invention is not necessarily limited thereto. The preferred amines for use herein have the formula $RNH_2$ where R is a hydrocarbyl group.

The amines being separated should have a difference in basicity constant of at least 1.5:1. The difference in partition between the aqueous phase and the organic phase is directly proportional to the basicity constant $K_B$ of the amines being separated. Thus for a given level of product purity the required number of stages in the multistage extraction apparatus being used must increase as the difference in the ratio of the basicity constants of the amines being separated decreases.

In a preferred aspect of the invention a hydrocarbon solvent is used to dissolve the free amines to facilitate separation of the organic and the aqueous phases when the density of the free amine is not sufficiently different from that of the aqueous phase of the sulfite salt. Suitable solvents are essentially immiscible with water. Preferred solvents are normally liquid hydrocarbons containing 5 to 12 carbon atoms.

EXAMPLE

In the following example all parts are by weight.

The apparatus schematically shown in the drawings is used to separate a mixture of toluidines containing 60% o-toluidine, 36% p-toluidine and 4% m-toluidine. When toluene is nitrated and then reduced to toluidine the above mixture of isomers results which cannot be separated by distillation because of the closeness of the boiling points of the three isomers. The three isomers cannot be separated by crystallization because after separation of some p-toluidine, both p-toluidine and o-toluidine will crystallize out. The o-toluidine isomer has a basicity constant $K_B$ of $2.6 \times 10^{-10}$, the p-toluidine isomer a basicity constant $K_B$ of $12 \times 10^{-10}$, and the m-toluidine isomer a basicity constant of $5 \times 10^{-10}$.

One hundred parts per hour of a mixture of 60% o-toluidine, 36% p-toluidine and 4% m-toluidine are fed by line 11 to a feed dissolver 12 maintained at 60° C. A stream 13 of toluene is fed at a rate of 233 parts per hour to feed dissolver 13. The resulting dissolved toluidine isomers are fed to a countercurrent extraction column 14 which has twenty-two theoretical stages. A recycle solution of about 40 wt % o-toluidine sulfite in water is fed at a rate of 662 parts per hour to the top of countercurrent extraction column 14. A recycle stream of about 30 wt % mixed p-toluidine and m-toluidine in toluene is fed to the bottom of countercurrent extraction column 14 at a rate of 367 parts per hour. A stream 17 of 30 wt % o-toluidine in toluene is removed from countercurrent extractor. A portion of this stream 17, 200 parts per hour is fed to washer 18 where it is washed with caustic fed by line 19. The effluent from washer 18 is fed to decanter 21 where the organic phase comprising o-toluidine and toluene is separated from the aqueous phase. The organic phase is fed to column 24 where toluene is recovered at a rate of 140 parts per hour in line 25 and 99.5% o-toluidine at a rate of 60 parts per hour in line 26. A stream of o-toluidine in toluene in line 30 is fed at a rate of 500 parts per hour to neutralizer 31. Water in line 32 is fed to neutralizer 31 at a rate of 422 parts per hour. Sulfur dioxide from sulfur dioxide regenerator 34, 66 parts per hour, and sulfur dioxide in line 35 from storage and sulfur dioxide regenerator of the secondary separation unit, 24 parts per hour, are fed in line 33 to neutralizer 31. The effluent from neutralizer 31 is fed to decanter 36 where toluene is removed in line 38 at a rate of 350 parts per hour. The o-toluene sulfite solution from decanter 36 is fed in line 15 to countercurrent extraction column 14 at a rate of 662 parts per hour.

A mixture of m-toluidine sulfite and p-toluidine sulfite is removed from countercurrent extraction column 14 in line 40 at a rate of 662 parts per hour. Part of the p-toluidine sulfite/m-toluidine sulfite solution is fed to sulfur dioxide regenerator at a rate of 486 parts per hour where it is heated to 100° C. to break down the sulfite salt and release sulfur dioxide. The resulting p-toluidine/m-toluidine mixture is fed to extractor 41 where it is mixed with toluene fed to extractor 41 in line 43 at a rate of 256 parts per hour. The mixture from extractor 41 is fed to decanter 45 where water is removed in line 46 at a rate of 310 parts per hour. The resulting solution of p-toluidine and m-toluidine in toluene is fed to countercurrent extractor 14 at a rate of 367 parts per hour.

A portion of the aqueous m-toluidine sulfite/p-toluidine sulfite solution in line 40 is taken in line 47 at a rate of 177 parts per hour and fed to countercurrent extraction column 50 which has twenty theoretical stages. A solution of m-toluidine in toluene is removed from countercurrent extractor 50 in line 53 and fed to neutralizer 54 at a rate of 227 parts per hour. Water is fed to neutralizer 54 at a rate of 191 parts per hour. Sulfur dioxide is fed to neutralizer 54 at a rate of 41 parts per hour in line 57. The effluent from neutralizer 54 is fed to decanter 59 where a stream of toluene is removed in line 60 at a rate of 159 parts per hour. The aqueous solution of m-toluidine sulfite is removed from decanter 59 and a portion is fed in line 62 to basifier 63 where it is treated with sodium hydroxide to free m-toluidine. The effluent from basifier 63 is fed to decanter 66 where it is separated into a stream of 98.5% m-toluidine in line 67 at a rate of 4 parts per hour and an aqueous stream in line 68 at a rate of 11 parts per hour. The remaining m-toluidine sulfite solution from decanter 59 is fed to countercurrent extractor 50 in line 51 at a rate of 283 parts per hour. An aqueous solution of p-toluidine sulfite is removed from countercurrent extractor 50 in line 70 and fed to sulfur dioxide regenerator 56 where it is heated to 100° C. to break down the p-toluidine sulfite and release sulfur dioxide at a rate of 62 parts per hour, 22 parts per hour of which are removed in line 71 and the remainder fed to neutralizer 54. The remaining p-toluidine and water is fed to decanter 73 where an aqueous phase is removed in line 78 and fed to extractor 77. The p-toluidine is removed from decanter 73 in line 74 where a product stream of 99.5% p-toluidine is removed in line 75 at a rate of 36 parts per hour. The remaining p-toluidine is fed in line 76 to extractor 77 at a rate of 68 parts per hour. Toluene in line 79 is fed to extractor 77 at a rate of 159 parts per hour. The effluent from extractor 77 is fed to decanter 81 where it is separated into an aqueous phase which is removed in line 82 at a rate of 250 parts per hour and a stream of p-toluidine in toluene which is fed in line 52 to countercurrent extractor 50 at a rate of 293 parts per hour.

I claim:

1. A process of separating two or more water immiscible amines having a basicity $K_B$ of from $1 \times 10^{-10}$ to $20 \times 10^{-10}$ and a difference in basicity $K_B$ of at least about 1.5:1 comprising (1) feeding a mixture of such amines to a mid point of a countercurrent extractor, (2) removing an organic phase containing the less reactive amine from one end of said countercurrent extractor, (3) recovering a portion of said less reactive amine, (4) neutralizing the remainder of said less reactive amine with sulfurous acid, (5) recycling the neutralized less reactive amine to said countercurrent extractor, removing an aqueous phase containing the acid salt of the more reactive amine(s) from said countercurrent extractor, (6) reforming the free more reactive amine(s) while recovering $SO_2$ which is used to neutralize the less reactive amine in step (4) above, (7) removing the aqueous phase from such free more reactive amine(s) (8) removing a portion of said more reactive amine(s) from the system, and (9) returning the remaining portion of such free amine(s) to said countercurrent extractor.

2. The process of claim 1 wherein a water immiscible solvent is mixed with the free amine prior to its being introduced into the countercurrent extractor.

3. The process of claim 2 wherein sulfur dioxide is regenerated by heating the more reactive amine sulfite when forming the free more reactive amine.

4. The process of claim 1 wherein the amines being separated is a mixture of toluidine isomers.

5. The process of claim 4 wherein a water immiscible solvent is mixed with the toluidines prior to their being fed to the countercurrent extractor.

6. The process of claim 5 wherein sulfur dioxide is regenerated by heating the more reactive toluidine sulfite when forming the free more reactive toluidine.

* * * * *